United States Patent [19]

Page et al.

[11] Patent Number: 4,877,559

[45] Date of Patent: Oct. 31, 1989

[54] NEW PROCESS FOR THE PREPARATION OF ALPHA-6-DEOXY-5-HYDROXYTETRACYCLINE

[75] Inventors: Philip R. Page, Parede; Ivan Villax, Lisboa, both of Portugal

[73] Assignee: Plurichenue Anstalt, Liechtenstein, Portugal

[21] Appl. No.: 925,109

[22] Filed: Oct. 27, 1986

Related U.S. Application Data

[60] Division of Ser. No. 732,952, May 13, 1985, which is a continuation-in-part of Ser. No. 458,068, Jan. 14, 1983, Pat. No. 4,550,096.

[30] Foreign Application Priority Data

Jan. 19, 1982 [PT] Portugal ................... 74.303
Dec. 30, 1982 [PT] Portugal ................... 76.061
Dec. 28, 1984 [PT] Portugal ................... 79.774

[51] Int. Cl.$^4$ .......................................... C07C 103/19
[52] U.S. Cl. .................................................. 552/204
[58] Field of Search ..................................... 260/351.5

[56] References Cited

U.S. PATENT DOCUMENTS

| | | | |
|---|---|---|---|
| 3,954,862 | 5/1976 | Morris, Jr. ........................ | 260/351.5 |
| 3,962,131 | 6/1976 | Faubl et al. ...................... | 260/351.5 |
| 4,001,321 | 1/1977 | Faubl ................................ | 260/351.5 |
| 4,031,137 | 6/1977 | Schmitt, Jr. et al. ............ | 260/351.5 |
| 4,207,258 | 6/1980 | Broggi et al. .................... | 260/351.5 |
| 4,500,458 | 2/1985 | Villax et al. ...................... | 260/351.5 |
| 4,550,096 | 10/1985 | Page et al. ....................... | 260/351.5 |
| 4,597,904 | 7/1986 | Page ................................. | 260/351.5 |

*Primary Examiner*—Richard L. Raymond
*Assistant Examiner*—Raymond Covington
*Attorney, Agent, or Firm*—Ostrolenk, Faber, Gerb & Soffen

[57] ABSTRACT

A homogenous hydrogenation process of preparing 6-demethyl-6-deoxy-6 methylene-5-hydroxytetracycline using a stereospecific tertiary phosphine-hydrozino-rhodium complex catalyst.

16 Claims, No Drawings

NEW PROCESS FOR THE PREPARATION OF ALPHA-6-DEOXY-5-HYDROXYTETRACYCLINE

This is a divisional application of application Ser. No. 732,952, filed May 13 1985 pending, which was itself a continuation-in-part of Ser. No. 458,068, now U.S. Pat. No. 4,550,096 filed on Jan. 14, 1983.

The present invention refers to a new improved process for the stereospecific hydrogenation of the 6-methylene group of an acid addition salt of 6-demethyl-6-deoxy-6-methylene-5-hydroxytetracycline to prepare α-6-deoxy-5-hydroxytetracycline (doxycycline), and to the subsequent recovery of pure doxycycline as p-toluenesulphonate directly from the reaction mixture in a nearly stoichiometric yield.

The α-isomer of 6-deoxy-5-hydroxytetracycline was first isolated in pure form and described in U.S. Pat. No. 3,200,149, applied for in 1960. Subsequently, a considerable number of patents referred to improved processes for preparing doxycycline. However, none of them was stereospecific and the yields obtained lay between 8 and 64% until the discovery of the first homogeneous hydrogenation process.

U.S. Pat. No. 4,207,258 (Italian priority 1972) describes such homogeneous hydrogenation of 6-demethyl-6-deoxy-6-methylenetetracyclines, using a complex of rhodium with tertiary phosphine, arsine and stibine ligands with predominant formation of the α-isomer.

Essentially the same process, equivalent to the above, is described in French Pat. No. 2,216,268 (U.S. priority 1973).

U.S. Pat. No. 3,954,862 (first filed in 1973) describes the hydrogenation of 6-demethyl-6-deoxy-6-methylenetetracyclines in the presence of rhodium metal, a tertiary phosphine and a promoter selected from strong acid or stannous chloride. Thus, this process prepares the catalyst, described in U.S. Pat. No. 4,207,258, in the reaction mixture, starting from rhodium metal and strong acid or stannous chloride, instead of the equivalent rhodium chloride.

Doxycycline is prepared by the transformation of 6-demethyl-6-deoxy-6-methylene-5-hydroxytetracycline, using cobalt carbonyl, triphenylphosphine and hydrochloric acid in U.S. Pat. No. 3,907,890 (filed in 1974).

U.S. Pat. No. 4,001,321 (filed in 1975) employs dicarboxylato (triphenylphosphine) rhodium (II) or dicarboxylato (substituted triphenylphosphine) rhodium (II) to produce doxycycline by hydrogenation.

U.S. Pat. No. 3,962,131 (filed in 1975) describes the preparation of a new catalyst by reacting rhodium trichloride and sodium acetate in methanol, followed by reaction with triphenylphosphine, and the hydrogenation of 6-demethyl-6-deoxy-6-methylene-5-hydroxytetracycline in its presence.

U.S. Pat. No. 4,500,458 describes the use of a homogeneous rhodium catalyst containing, besides a tertiary phosphine, a hydrazine as a ligand. The incorporation of a hydrazine as a ligand into the complex has the unexpected result of improving the regiospecificity and stereospecificity of the catalyst for the hydrogenation of exocyclic methylene groups, such as for instance in the hydrogenation of methacycline to α-6-deoxy-5-hydroxytetracycline. A significant reduction in the amount of catalyst employed in relation to the substrate, as well as a reduction of the pressure and reaction time are achieved. The process described therein has been found not to use a catalyst in a completely pure form, i.e. the catalyst is contaminated by oxygen absorbed during its preparation. The catalysts used in the present invention are prepared substantially free of this type of contamination, as is more fully described in the co-pending Patent Application Ser. No. 732,952.

The present invention relates to the use of new homogeneous rhodium catalysts, the preparation of which is described in the co-pending Patent Application Ser. No. 732,952.

These new catalysts are obtained by reacting a rhodium salt, preferably rhodium chloride, a tertiary phosphine, preferably triphenylphosphine, and an eventually substituted hydrazine, preferably hydrazine hydrate, in a degassed reaction inert solvent under an inert atmosphere. Alternatively, these catalysts can be prepared by reacting a known complex of rhodium and of a tertiary phosphine with a hydrazine in a degassed reaction inert solvent under an inert atmosphere. These nitrogen containing new rhodium catalysts are stereospecific, yielding nearly exclusively the α-isomer in the hydrogenation of methacycline.

Thus, the present invention concerns the preparation of α-6-deoxy-5-hydroxytetracycline by hydrogenating a compound of the formula:

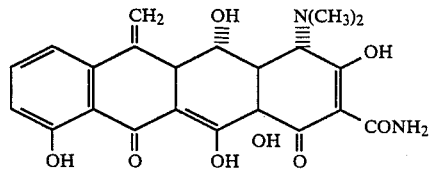

in a reaction inert solvent, in the presence of a tertiary phosphine-hydrazino-rhodium complex as catalyst.

As is taught in the co-pending Patent Application Ser. No. 732,952, two of the catalysts prepared therein have been structurally identified. The structures are as follows:

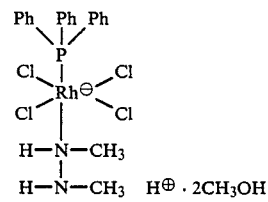

.../...

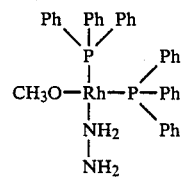

wherein Ph represents a phenyl group.

The use of these two catalysts is a preferred embodiment of the present invention, especially the use of the bis(triphenylphosphine)hydrazinomethoxyrhodium (I).

The pressure is not critical; it can be from atmospheric pressure upwards, however the preferred pressure range is from 1 to 10 kg/cm². The hydrogenation is carried out preferably at a temperature range from about 20° C. to 95° C., preferentially within the range from about 60° C. to 90° C. At low temperatures the reaction is too slow, and above 100° C. decomposition starts to take place.

The reaction time is dependent on the amount of catalyst used and type of high pressure reaction vessel. A satisfactory reaction time is from about 3 to 10 hours, although satisfactory results and high yields can be obtained even after 16 hours of hydrogenation.

The starting material, 6-demethyl-6-deoxy-6-methylene-5-oxytetracycline (methacycline), can be prepared by any of the known processes, such as that described in U.S. Pat. No. 3,849,491, but should not contain impurities which may act as a catalyst inhibitor.

It is added in the form of an acid addition salt, such as the hydrochloride or the p-toluenesulphonate, but other acid addition salts can be used, provided that the acid is not a catalyst inhibitor.

The hydrogenation is stopped when the rate of consumption of hydrogen drops drastically. The reaction mixture, once the hydrogenation is completed, containing nearly exclusively the α-isomer, does not contain unreacted starting material or only traces; the amount of by-products or degradation products is negligible and the β-isomer is less than 1%, usually it is around 0.1%.

The purity of the reaction mixture thus obtained is such that the doxycycline can be crystallised directly from the reaction mixture by adding p-toluenesulphonic acid in excess, on condition that the solvent in the reaction medium is a non-solvent for the p-toluenesulphonate salt of doxycycline thus formed; such a solvent is preferably methanol. The purity so obtained is normally superior to 99% calculated on the dry basis.

The doxycycline p-toluenesulphonate can subsequently be transformed directly into the hydrochloride hemiethanolate hemihydrate by conventional processes with a yield near to stoichiometric.

Another feature of the present invention is that the amount of rhodium necessary to achieve complete reaction is very reduced, therefore making the process very economical. Table I compares the amount of catalyst expressed as rhodium, yields and purities of the best examples of the prior art processes compared with those of the present invention.

This table shows clearly that the present invention is similar to that of U.S. Pat. No. 4,500,458, over which it represents an improvement in that the catalyst structures are known, thereby allowing easy determination of the optimal quantity of catalyst to be used. In respect of the other prior art processes, the present invention requires less rhodium to produce higher and more stereospecific yields of α-6-deoxy-5-hydroxytetracycline.

TABLE I

| Patent | Example | Starting material | Noble Metal | Amount of noble metal per g Mot (mg) | Stoichiometric yield of product | Analysis of Product | | | | Stoichiometric yield of pure doxycycline |
|---|---|---|---|---|---|---|---|---|---|---|
| | | | | | | α-epimer | β-epimer | Mot | Decomp. Products | |
| U.S. Pat. No. 4,207,258 | 1 | Mot HCl | Rh | 26.5 | N.I. | 95.0%ϕ | 5.0%ϕ | N.I. | Traces | 73.2%ⲑ |
| | 2 | Mot HCl | Rh | 21.2 | N.I. | 95.0%ϕ | 5.0%ϕ | N.I. | Traces | 74.6%ⲑ |
| | 3 | Mot HCl | Rh | 26.5 | N.I. | N.I. | N.I. | N.I. | N.I. | 71.9%ⲑ |
| French Patent 2,216,268 | 1 | Mot | Rh | 132.3 | 85.0% | 92.0%ϕ | 8.0%ϕ | N.I. | N.I. | 78.2%ϕ |
| | 2 | Mot | Rh | 132.3 | 70.0% | 71.0%ϕ | 29.0%ϕ | N.I. | N.I. | 49.7%ϕ |
| | 3 | Mot HCl | Rh | 23.0 | 90.6% | 95.0%ϕ | 0.7%ϕ | N.I. | N.I. | 86.0%ϕ |
| | 5 | Mot HCl | Rh | 2.3 | 89.2% | N.I. | 0.6% | 0% | N.I. | N.I. |
| | 9 | Mot HCl | Rh | 0.6 | 78.4%Φ | 78.4%Φ | 0.8%Φ | 5.2%Φ | 15.6%Φ | 61.5%Φ |
| U.S. Pat. No. 3,954,862 | 3 | Mot HCl | Rh | 2.3 | 80.0% | 81.0%ϕ | 1.6%Φ | N.I. | N.I. | 64.8% |
| | 4 | Mot HCl | Rh | 23.0 | 78.0% | 80.0%ϕ | 1.5%ϕ | N.I. | N.I. | 62.4% |
| U.S. Pat. No. 4,001,321 | 1 | Mot HCl | Rh | 10.1 | 94.7% | 93.0%ⲑ | 2.0–3.0%ϕ | N.I. | N.I. | 88.1% |
| U.S. Pat. No. 3,962,131 | 2 | Mot HCl | Rh | <3.6 | 98.6% | 99.7%ⲑ | N.I. | N.I. | N.I. | 98.4% |
| U.S. Pat. No. 3,907,890 | 5 | Mot HCl | Co | 268.6 | 75.2% | 98.0% | 2.0% | 0% | N.I. | 73.7% |
| U.S. Pat. No. 4,500,458 | 2 | Mot HCl | Rh | 0.37 | 90.2% | 99.5% | 0.45% | Traces | 0% | 89.7% |
| | 4 | Mot HCl | Rh | 0.67 | 99.1% | 99.89% | 0% | 0% | Slight traces | 99.0% |
| Present invention | 1 | Mot HCl | Rh | 0.60 | 92.4% | 99.4% | 0% | 0% | N.I. | 91.8% |
| | 3 | Mot HCl | Rh | 0.55 | 93.7% | 99.5% | 0% | 0% | N.I | 93.2% |

Notes:
Mot — 6-demethyl-6-deoxy-6-methylene-5-hydroxy-tetracycline.
HCl — hydrochlorid acid.
ϕ - content from analysis of the reaction mixture.
Φ - based upon both fractions obtained.
ⲑ - content from U.V. analysis.
N.I. — not indicated.

It has been observed that the addition of a small amount of a tertiary phosphine (preferably the same one as contained in the catalyst used) to the reaction mixture, prior to starting the hydrogenation, will accelerate the rate of hydrogen consumption, facilitate completion of the reaction and increase the yield up to nearly stoichiometric. The preferred excess of the tertiary phosphine in relation to the catalyst is about 10 moles/mole, although it can be increased to above 50 moles/mole without detriment to the yield or purity of the product. The optimal amount of additional tertiary phosphine can be easily determined for a given catalyst by running a few experiments.

The results clearly show the unexpected superiority of the new tertiary phosphine-hydrazino-rhodium complexes as hydrogenation catalysts not only concerning yields and purity, but also in reducing the amount of rhodium necessary to complete the hydrogenation in relation to the prior art processes. The tertiary phosphine-hydrazino-rhodium complexes and their preparation are described in the co-pending Patent Application Ser. No. 732,952.

These new catalysts can be prepared either from a rhodium salt or from an already known tertiary phosphine rhodium complex.

Thus, a tertiary phosphine rhodium complex (1 mole) is reacted with an excess of hydrazine, substituted or not. A preferred catalyst can be prepared by reacting tris(triphenylphosphine)chlororhodium (I) (1 mole) with an excess of hydrazine hydrate (3 moles) by stirring at room temperature in degassed methanol under a nitrogen atmosphere.

Alternatively, rhodium trichloride trihydrate (1 mole), a tertiary phosphine (about 4 moles) and an excess of hydrazine (about 3 moles) are reacted, eventually by heating or refluxing them in a degassed reaction inert solvent, such as a lower dialkyletone, lower alcohol, tetrahydrofuran, dioxan or dimethylformamide under a nitrogen atmosphere.

The following examples serve to illustrate the present invention, without in any way limiting the scope thereof.

EXAMPLE 1

Catalyst: Tris(triphenylphosphine)chlororhodium (I) (0.5 g; 0.54 mmoles) was refluxed under a nitrogen atmosphere with N,N'-dimethylhydrazine dihydrochloride (0.215 g; 1.62 mmoles) in dry, degassed methanol (30 ml) for 90 minutes. The colour of the reaction mixture changed from purple-red to orange during this time. On cooling, a product crystallised which was filtered, washed and dried. A second fraction could be obtained by addition of degassed di-isopropyl ether to the mother liquors.

The X-ray diffraction data were recorded using an Enraf-Nonius CAD4 diffractometer and Ni-filtered Cu-K$\alpha$ radiation ($\lambda$=1.54178 Å), following standard procedures. The details of the analysis were as follows:

1. Crystal data: [RhCl$_4$(NHMe.NHMe)(PPh$_3$)]$^\ominus$.2C-H$_3$OH.(H$^\oplus$). C$_{22}$H$_{32}$Cl$_4$N$_2$O$_2$PRh; M=632.17; triclinic; space group P1; a=16.430(3) Å, b=9.848(2) Å, c=9.850(2) Å; $\alpha$=117.79(2)°, $\beta$=75.99(2)°, $\gamma$=95.15(2)°; U=1367.5 Å$^3$; Z=2; $\mu$(Cu-K$\alpha$)=50.30 cm$^{-1}$.

2. Data collection was in $\omega/2\theta$ scan mode, 3°$\leq\theta\leq$60°, and T=293° K. 4047 data were recorded, of which 3491 were independant and satisfied the condition I>1.5$\sigma$ (I) and were used in the analysis.

3. Structure analysis was solved by the heavy atom method, and refined by the least-squares method. All non-hydrogen atoms were refined with anisotropic thermal parameters, phenyl rings being treated as rigid bodies, with hydrogen atoms included in idealised positions. Some hydrogens on the hydrazine and methanol moieties were located on difference electron-density maps and were refined, with individual isotropic thermal parameters. The final R value was 0.0393.

Further analytical values on the product were as follows:

I.R. (KBr disc) 2.86, 3.28, 6.20, 6.35, 6,75, 7.00, 7.16, 8.40, 9.17, 13.35 and 14.35 microns.

Elemental analysis Calculated content: Rh-16.30%; N-4.44% Found content: Rh-16.13%; N-4.57%.

Hydrogenation: 25 mg (39.54 $\mu$moles) of the thus obtained catalyst in methanol (20 ml) was added to a stainless steel high pressure reaction vessel under magnetic stirring, containing 6-demethyl-6-deoxy-6-methylene-5-hydroxytetracycline hydrochloride (7.38 g; 15.41 mmoles) and triphenylphosphine (0.1 g; 0.38 mmoles) in methanol (40 ml). After purging it with nitrogen, hydrogen was added to a pressure of 8 kg/cm$^2$ and the reaction mixture was heated up to 89° C. After 5 h 30 m the consumption dropped, and 1 hour later the reaction mixture was cooled down. It was filtered through a G4 glass-filter, then p-toluenesulphonic acid (3.3 g; 17.35 mmoles) was added to the filtrate which was then stirred. The $\alpha$-6-deoxy-5-hydroxytetracycline p-toluenesulphonate thus formed was filtered, washed with acetone and dried. The product weighed 8.78 g, and had a purity of 99.4%. No $\beta$-isomer or starting material were detectable by circular paper chromatography ("Schleicher & Schüll" paper No. 2045 B, 265 nm, ref. No. 381804; stationary phase: 100 ml of a solution of 0.1M citric acid and 40 ml of 0.2M anhydrous disodium phosphate were mixed to make a buffer with pH 3.5; mobile phase: nitromethane:chloroform:pyridine-20:10:3).

EXAMPLE 2

Catalyst: Rhodium trichloride trihydrate (0.527 g; 2.00 mmoles) and triphenylphosphine (2.098 g; 8.00 mmoles) were refluxed under nitrogen in dry, degassed methanol (10 ml) for 1 hour. Then N,N'-dimethylhydrazine dihydrochloride (0.798 g; 6.00 mmoles) was added and the reflux continued for a further hour. After slow cooling, the crystalline product was filtered, washed and dried. It was analytically identical with the compound prepared in Example 1.

Hydrogenation: 25 mg (39.54 $\mu$moles) of the thus obtained catalyst in methanol (20 ml) was added to a stainless steel high pressure reaction vessel under magnetic stirring, containing 6-demethyl-6-deoxy-6-methylene-5-hydroxytetracycline hydrochloride (7.38 g; 15.41 mmoles) in methanol (40 ml). Following the operating conditions given in Example 1, $\alpha$-6-deoxy-5-hydroxytetracycline p-toluenesulphonate was obtained, weighing 8.30 g. The purity was 99.5% of $\alpha$-epimer, with no starting material being detectable.

EXAMPLE 3

Catalyst: Tris(triphenylphosphine)chlororhodium (I) (0.48 g; 0.52 mmoles) was refluxed under nitrogen for 90 minutes with hydrazine hydrate (76 $\mu$l; 1.56 mmoles) in dry, degassed methanol (20 ml). The yellow orange solution was cooled to yield a yellow solid.

The infra-red spectrum of this yellow solid showed the presence of triphenylphosphine, contained a band around 3300 cm$^{-1}$ due to the stretching of the N—H bonds and a band at 420–430 cm$^{-1}$ due to the presence of the metal bonded methoxy group. There was no band in the 250–400 cm$^{-1}$ region that could be assigned to a rhodium-chlorine bond (as compared with the band at 320 cm$^{-1}$ for the Wilkinson catalyst). Additionally, the absence of chlorine in the compound was confirmed by a negative spot test. The nuclear magnetic resonance spectrum showed one sharp peak at $\delta$3.4, assigned to the protons of the methoxy group and a complex region at $\delta$7–7.5 due to the protons of the phenyl groups. The mass spectrum did not show a molecular ion, the highest peak being for Rh(PPh$_3$)$_2$. These results show the structural identity of the compound to be bis(triphenylphosphine)hydrazinomethoxyrhodium (I).

Hydrogenation: The conditions of the hydrogenation of Example 1 were repeated using the catalyst obtained above (25 mg; 36.20 $\mu$moles) to yield 8.90 g of $\alpha$-6-deoxy-5-hydroxytetracycline p-toluenesulphonate, with a content of 99.5% of the $\alpha$-epimer. No $\beta$-epimer or starting material were detectable by circular chromatography.

We claim:

1. A new improved homogeneous hydrogenation process to prepare α-6-deoxy-5-hydroxytetracycline in high yield and purity from a 6-demethyl-6-deoxy-6-methylene-5-hydroxytetracycline acid addition salt in the presence or absence of a tertiary phosphine by stereospecific catalytic hydrogenation, characterised in that the catalyst is a new tertiary phosphinehydrazinorhodium complex obtained by reacting a rhodium salt or a complex with a hydrazine or salt thereof, at a pressure of 1 to 10 kg/cm$^2$ and a temperature from 20° C. to 95° C. in the presence of a solvent inert in the reaction, and subsequently the pure α-6-deoxy-5-hydroxytetracycline formed is recovered directly from the reaction mixture as crystalline p-toluenesulphonate by addition of an excess of p-toluenesulphonic acid.

2. Process according to claim 1, wherein for each part of substrate to be hydrogenated the amount of rhodium metal in the catalyst necessary to perform the hydrogenation is less than 0.0007 parts.

3. Process according to claim 1, wherein the catalyst is trans-tetrachloro-N,N'-dimethylhydrazino(triphenylphosphine)rhodium (III) acid dimethanolate.

4. A process according to claim 1, wherein the catalyst is bis(triphenylphosphine)hydrazinomethoxyrhodium (I).

5. Process according to claim 1, wherein the rhodium salt or complex is tris(triphenylphosphine)chlororhodium and the hydrazine or salt thereof is hydrazine.

6. Process according to claim 1, wherein the rhodium salt or complex thereof is rhodium trichloride trihydrate and the hydrazine or salt thereof is hydrazine.

7. Process according to claim 1, wherein the 6-demethyl-6-deoxy-6-methylene-5-hydroxytetracycline acid addition salt is hydrogenated in the presence of said catalyst and about 10 moles of tertiary phosphine per mole of the catalyst employed.

8. Process according to claim 7, wherein the tertiary phosphine in the catalyst and the additional tertiary phosphine in which the reaction is carried out in the presence of are the same.

9. Process according to claim 1, wherein the pure α-6-deoxytetracycline formed is recovered directly from the reaction mixture as crystalline p-toluenesulphonate by addition of an excess of p-toluenesulphonic acid.

10. Process according to claim 2, wherein the pure α-6-deoxytetracycline formed is recovered directly from the reaction mixture as crystalline p-toluenesulphonate by addition of an excess of p-toluenesulphonic acid.

11. Process according to claim 3, wherein the pure α-6-deoxytetracycline formed is recovered directly from the reaction mixture as crystalline p-toluenesulphonate by addition of an excess of p-toluenesulphonic acid.

12. Process according to claim 4, wherein the pure α-6-deoxytetracycline formed is recovered directly from the reaction mixture as crystalline p-toluenesulphonate by addition of an excess of p-toluenesulphonic acid.

13. Process according to claim 5, wherein the pure α-6-deoxytetracycline formed is recovered directly from the reaction mixture as crystalline p-toluenesulphonate by addition of an excess of p-toluenesulphonic acid.

14. Process according to claim 6, wherein the pure α-6-deoxytetracycline formed is recovered directly from the reaction mixture as crystalline p-toluenesulphonate by addition of an excess of p-toluenesulphonic acid.

15. Process according to claim 7, wherein the pure α-6-deoxytetracycline formed is recovered directly from the reaction mixture as crystalline p-toluenesulphonate by addition of an excess of p-toluenesulphonic acid.

16. Process according to claim 8, wherein the pure α-6-deoxytetracycline formed is recovered directly from the reaction mixture as crystalline p-toluenesulphonate by addition of an excess of p-toluenesulphonic acid.

* * * * *